(12) United States Patent
Cai

(10) Patent No.: US 11,377,181 B2
(45) Date of Patent: Jul. 5, 2022

(54) LIFE-SAVING DEVICE FOR USE IN WATER

(71) Applicant: Xinyong Cai, Shaoxing (CN)

(72) Inventor: Xinyong Cai, Shaoxing (CN)

(*) Notice: Subject to any disclaimer, the term of this patent is extended or adjusted under 35 U.S.C. 154(b) by 143 days.

(21) Appl. No.: 17/035,797

(22) Filed: Sep. 29, 2020

(65) Prior Publication Data

US 2021/0009246 A1 Jan. 14, 2021

Related U.S. Application Data

(63) Continuation-in-part of application No. PCT/CN2019/120919, filed on Nov. 26, 2019.

(30) Foreign Application Priority Data

Dec. 21, 2018 (CN) .......................... 201811572389.1

(51) Int. Cl.
*B63C 9/15* (2006.01)
*H02S 10/40* (2014.01)
*H02S 40/38* (2014.01)
*A61B 5/00* (2006.01)
*B63C 9/18* (2006.01)
*B63C 9/20* (2006.01)

(52) U.S. Cl.
CPC ............ *B63C 9/155* (2013.01); *A61B 5/6887* (2013.01); *A61B 5/746* (2013.01); *B63C 9/18* (2013.01); *B63C 9/20* (2013.01); *H02S 10/40* (2014.12); *H02S 40/38* (2014.12)

(58) Field of Classification Search
CPC .. B63C 9/155; B63C 9/18; B63C 9/20; H02S 10/40; H02S 40/38; A61B 5/746
See application file for complete search history.

(56) References Cited

U.S. PATENT DOCUMENTS

| | | | |
|---|---|---|---|
| 4,559,864 A * | 12/1985 | Sakakibara .......... | B60K 31/107 123/360 |
| 2003/0085024 A1* | 5/2003 | Santiago ............ | B01D 19/0031 257/E23.098 |
| 2009/0126482 A1* | 5/2009 | Fundak .................. | B63C 11/02 340/612 |
| 2016/0008811 A1* | 1/2016 | Laser .................. | B01L 3/50273 536/25.4 |
| 2021/0009246 A1* | 1/2021 | Cai .......................... | B63C 9/18 |

* cited by examiner

*Primary Examiner* — S. Joseph Morano
*Assistant Examiner* — Jovon E Hayes
(74) *Attorney, Agent, or Firm* — Matthias Scholl P.C.; Matthias Scholl

(57) ABSTRACT

A life-saving device, including: a buoyancy bag including a cavity; a wearable member including a housing; a controller including a single-chip microcomputer, a battery, a flip-flop, and an integrated circuit board; a gas generator including an input electrode terminal and a gas outlet. The single-chip microcomputer includes a plurality of pins and is disposed on the integrated circuit board; the battery, the flip-flop, and the input electrode terminal of the gas generator are respectively connected to the plurality of pins through the integrated circuit board; the housing includes a first chamber, and the battery, the single-chip microcomputer, and the integrated circuit board are disposed in the first chamber; the cavity of the buoyancy bag communicates with the gas outlet; and the buoyancy bag is deflated when in nonuse for convenience of storage, and inflated with gas produced by the gas generator to expand in an emergency.

18 Claims, 7 Drawing Sheets

LIFE-SAVING DEVICE FOR USE IN WATER

CROSS-REFERENCE TO RELATED APPLICATIONS

This application is a continuation-in-part of International Patent Application No. PCT/CN2019/120919 with an international filing date of Nov. 26, 2019, designating the United States, now pending, and further claims foreign priority benefits to Chinese Patent Application No. 201811572389.1 filed on Dec. 21, 2018. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to a life-saving device for use in water.

The life-saving devices in water include life-jackets, lifebuoys, swimming buoyancy bags. In general, these devices are made of buoyant materials and are inflated with air. As a result, the devices are bulky and occupy much space in the carrying process.

SUMMARY

The disclosure provides a life-saving device comprising a buoyancy hag, and a wearable member secured to a user or to a wearing apparel of the user. The buoyancy bag is deflated when in nonuse for convenience of storage, and inflatable with gas to expand in an emergency. The buoyancy bag is connected to the wearable member. The life-saving device further comprises a controller and a gas generator comprising a gas outlet. The wearable member comprises a housing. The controller comprises a single-chip microcomputer, a battery, a flip-flop and an integrated circuit board. The single-chip microcomputer comprises a plurality of pins and is disposed on the integrated circuit board. The battery, the flip-flop and the gas generator are respectively connected to the plurality of pins of the single-chip microcomputer through the integrated circuit board. The housing comprises a first chamber and the battery, the single-chip microcomputer, and the integrated circuit board are disposed in the first chamber. The buoyancy bag comprises a cavity communicating with the gas outlet. When a user falls into water, the flip-flop produces and transmits a signal to the single-chip microcomputer; the single-chip microcomputer controls the gas generator to produce gas entering the buoyancy bag. The buoyancy bag is inflated with the gas, expands and produces buoyancy to saving the user from drowning in the water.

In a class of this embodiment, the flip-flop is a pressure sensor, a delay trigger, a manual switch, or a combination thereof. The flip-flop is disposed outside the housing. The pressure sensor senses the water pressure and automatically transmits the measured data to the single-chip microcomputer which utilizes a series of preset values to determine the depth of water at the user's position. The decision whether to control the gas generator to generate the gas depends on the analysis result of the single-chip microcomputer. When the water flows over the delay trigger, the delay trigger is triggered in a short time and automatically transmits a signal to the single-chip microcomputer. The manual switch is a trigger switch used to transmit the signal to the single-chip microcomputer that controls whether the gas generator generates gas.

In a class of this embodiment, the controller further comprises a low-potential alarm connected to the single-chip microcomputer via the integrated circuit board. The low-potential alarm is disposed outside the housing, and is configured to produce an alarm signal when the capacity of the battery is below a set value.

In a class of this embodiment, the controller further comprises a wireless signal transmitter disposed in the first chamber of the housing or outside the housing, and functions to send out a distress signal or a communication signal.

In a class of this embodiment, the controller further comprises a solar generation mechanism disposed outside the housing. The integrated circuit board further comprises a power switching circuit. The solar generation mechanism and the battery are connected to the single-chip microcomputer through the power switching circuit. The solar generation mechanism is a substitute for the battery as a power source of the life-saving device.

In a class of this embodiment, the controller further comprises a human health monitoring sensor disposed outside the housing. The human health monitoring sensor is configured to monitor fitness features and assist in the diagnosis of human health on the basis of monitored data.

In a class of this embodiment, the life-saving device further comprises a timer, a pedometer, or a combination thereof. The timer and the pedometer are disposed in the first chamber of the housing, and connected to the single-chip microcomputer through the integrated circuit board. The life-saving device further comprises a display disposed outside the housing and connected to the single-chip microcomputer through the integrated circuit board. The display is an electronic device for the visual presentation of data recorded by the timer or the pedometer.

In a class of this embodiment, the wearable member further comprises an annular body connected to the housing. The wearable member is wrapped around the wrist or the arm of the user through the annular body.

In a class of this embodiment, the housing or the annular body comprises a second chamber to accommodate the buoyancy bag.

In a class of this embodiment, the gas generator is disposed in the buoyancy bag.

In a class of this embodiment, the gas generator is disposed inside the second chamber but outside the buoyancy bag.

In a class of this embodiment, the gas generator comprises an electronic igniter, a gas-generating agent, and a container; the gas-generating agent is disposed in the container. The electronic igniter is disposed in the container filled with the gas-generating agent. The container comprises the gas outlet communicating with the cavity of the buoyancy bag. The input electrode terminal is disposed on the electronic igniter and is connected to the electrode pin of the single-chip microcomputer through the integrated circuit board.

In a class of this embodiment, the second chamber and the buoyancy bag are annular in shape and match each other.

In a class of this embodiment, the annular body of the wearable member is a watchstrap; the housing of the wearable member is a watchcase; the watchcase comprises an accommodation chamber to accommodate a dial and a movement.

In a class of this embodiment, the annular body of the wearable member is a belt body; the housing of the wearable member is a belt buckle comprising a base; a connecting mechanism, and a locking mechanism; the base is connected to one end of the belt body via the connecting mechanism; and the first chamber and the second chamber are disposed in the base.

In a class of this embodiment, the buoyancy bag is connected to one end of a rope, and the other end of the rope is fixedly connected to the belt body or the belt buckle.

In a class of this embodiment, the wearable member further comprises a collar body and a connector secured to the collar body; the second chamber is disposed in the collar body; the gas producer is disposed in the buoyancy bag or disposed outside the buoyancy bag but inside the collar body.

In a class of this embodiment, the connector is a zipper.

In a class of this embodiment, the wearable member further comprises a connector; the buoyancy bag is a collar body secured to the connector; and the gas producer is disposed in the collar body.

In a class of this embodiment, the housing is a clothing accessory; the wearable member further comprises a connector secured to the clothing accessory; the gas producer is disposed in the buoyancy bag or disposed outside the buoyancy bag but inside the second chamber.

In a class of this embodiment, the clothing accessory is a badge, an epaulette or an armband.

In a class of this embodiment, the connector is a pin, a hook-and-loop fastener, or a tear tape.

The following advantages are associated with the life-saving device of the disclosure: the buoyancy bag is deflatable for convenience of storage, and inflatable to expand in an emergency to increase the buoyance of the buoyancy bag. Beneath the surface of the water, the electronic igniter automatically activates the gas-producing agent to produce gas in case of emergency to inflate the buoyancy bag. The advantages associated with the life-saving device of the disclosure include easy carrying and convenient usage. The life-saving device is multifunctional, the functions including giving a loud alarm at low potential, generating solar energy, monitoring human health, automatically sending a distress signal or a communication signal, measuring time intervals, and recording the number of steps taken.

Figure 1:
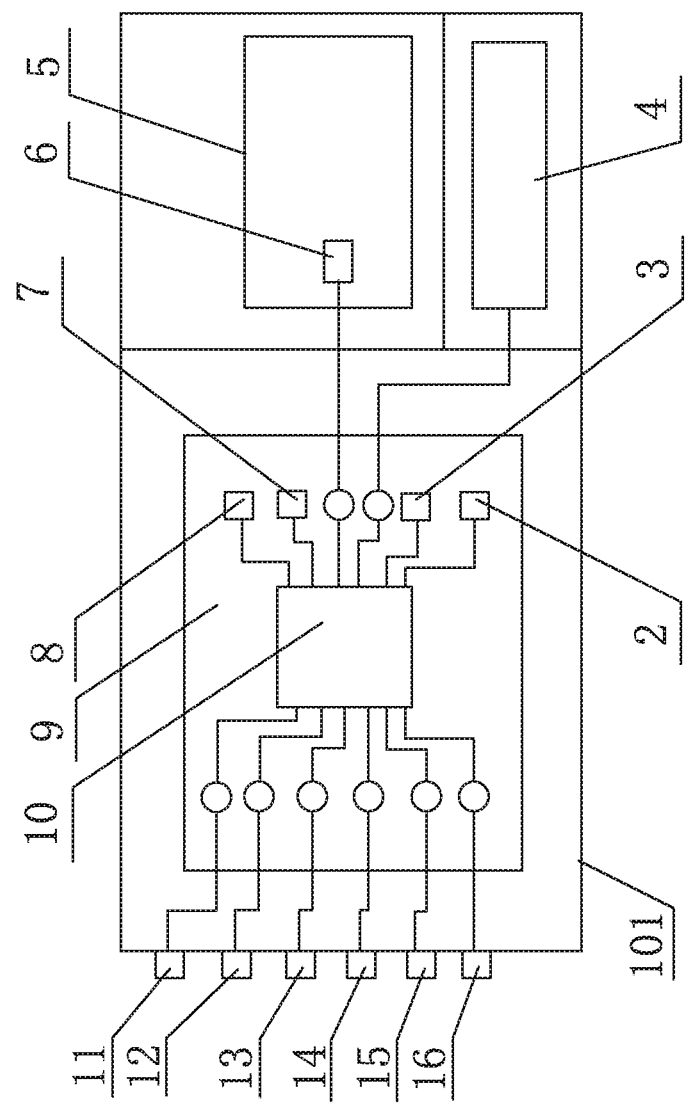
FIG. 1 is a front view of a life-saving device according to one embodiment of the disclosure.

In the drawings; the following reference numbers are used: 1. Wearable member; 101. Housing; 102. Annular body; 2. Timer; 3. Pedometer; 4. Display; 5. Buoyancy bag; 6. Gas generator; 7. Wireless signal transmitter; 8. Battery; 9. Integrated circuit board; 10. Single-chip microcomputer; 11. Solar generation mechanism; 12. Human health monitoring sensor; 13. Low-potential electronic siren; 14. Pressure sensor; 15. Delay trigger; 16. Manual switch; 17. Dial; 18, Crown; 19, Collar body; 20. Marker bar; 21. Belt body; 61. Container; 62. Electronic igniter; 64. Gas-producing agent; and 65. Gas outlet.

DETAILED DESCRIPTION

To further illustrate the disclosure, embodiments detailing a life-saving device are described below. It should be noted that the following embodiments are intended to describe and not to limit the disclosure.

Figure 2:
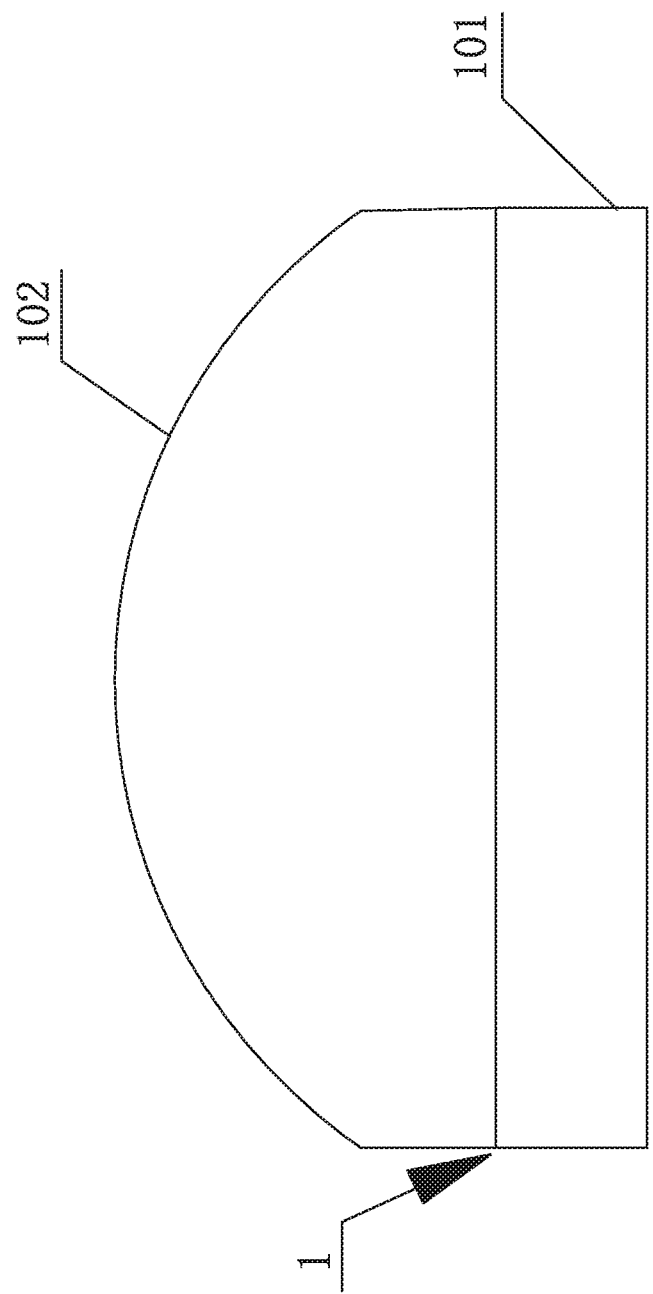
FIG. 2 is a top view of a life-saving device according to one embodiment of the disclosure.
Figure 3:
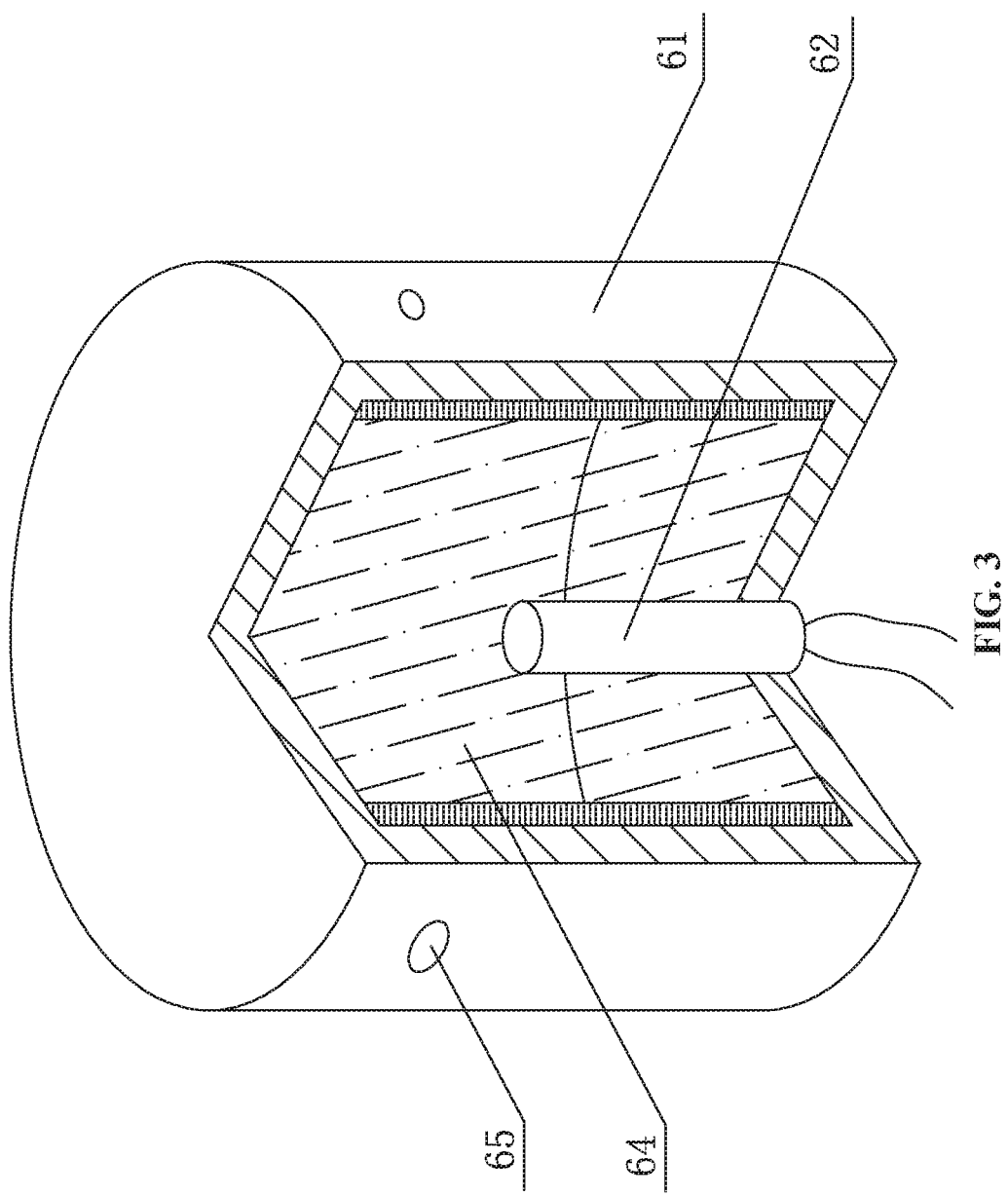
FIG. 3 is a schematic view of a gas generator according to one embodiment of the disclosure.

As shown in FIGS. 1, 2 and 3, the disclosure provides a life-saving device comprising a buoyancy bag 5, a wearable member 1, a controller; and a gas generator 6. The buoyancy bag 5 is deflated when in nonuse for convenience of storage, and inflatable with gas to expand in an emergency. The wearable member 1 comprises a housing 101 and an annular body 102 connected to the housing 101. The housing 101 comprises a first chamber and a second chamber. The controller comprises a single-chip microcomputer 10, a battery 8, a flip-flop, an integrated circuit board 9, a timer 2, a pedometer 3, a display 4, a wireless signal transmitter 7, a solar generation mechanism 11, a human health monitoring sensor 12, and a low-potential electronic siren 13. The integrated circuit board 9 comprises a power switching circuit, and is fixedly disposed in the first chamber of the housing 101. The single-chip microcomputer 10 is disposed on the integrated circuit board 9. The timer 2, the pedometer 3, and the wireless signal transmitter 7 are disposed on the integrated circuit board, and connected to the corresponding pins of the single-chip microcomputer through the integrated circuit board, respectively. The battery 8 and the solar generation mechanism 12 are connected to the single-chip microcomputer 10 through the power switching circuit. The single-chip microcomputer 10, the timer 2, the pedometer 3, the wireless signal transmitter 7 and the battery 8 are disposed in the first chamber of the housing 1, while the solar generation mechanism 11 is disposed outside the housing 101.

The flip-flop is a pressure sensor 14, a delay trigger 15, a manual switch 16, or a combination thereof. The pressure sensor 14, the delay trigger 15, the manual switch 16, the low-potential electronic siren 13, and the human health monitoring sensor 12 are disposed outside the housing 101, and connected to the corresponding pins of the single-chip microcomputer 10 through the integrated circuit board 9. The housing 101 comprises a third chamber configured to receive the display 4. The display 4 is connected to the corresponding pin of the single-chip microcomputer 10 through the integrated circuit board.

The housing 101 further comprises a hole through which the second chamber communicates with the external environment. The deflated buoyancy bag is disposed in the second chamber, and the buoyancy bag further comprises an inlet and a cavity. When an emergency situation occurs, the buoyancy bag is inflated rapidly and comes out of the second chamber of the housing 101. The gas generator 6 is disposed in the cavity of the buoyancy bag 5, and comprises an electronic igniter 62, a gas-producing agent 64, and a container 61 used to hold the gas-producing agent 64. The electronic igniter 62 is disposed in the container 61 filled with the gas-generating agent 64. The container 61 comprises a gas outlet 65 through which the cavity of the buoyancy bag 5 communicates with the container 61. The input electrode terminal of the electronic igniter 62 is connected to the electrode pin of the single-chip microcomputer 10 through the integrated circuit board 9.

In certain embodiments, when the second chamber is located in the annular body 102, the buoyancy bag and the second chamber are annular in shape and match each other.

The gas generator 6 is disposed in the buoyancy bag, or disposed inside the second chamber but outside the buoyancy bag. The gas outlet 65 of the container 61 communicates with the inlet of the buoyancy bag.

Figure 4:
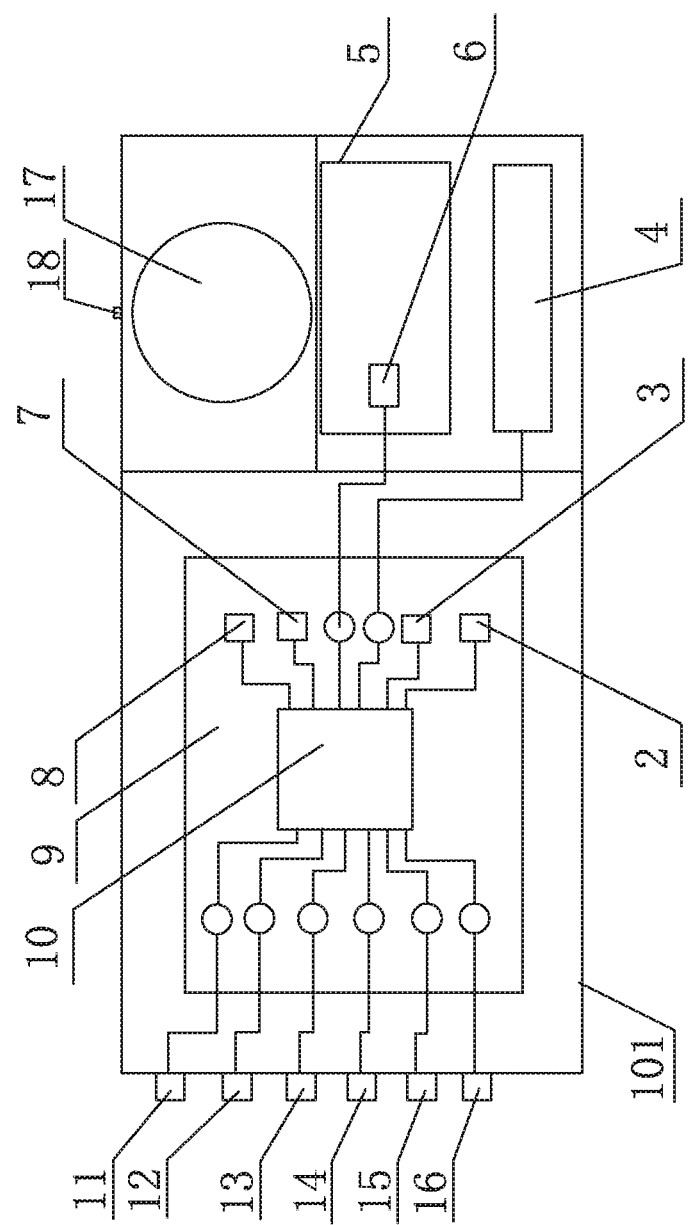
FIG. 4 is a front view of a watch comprising a life-saving device according to one embodiment of the disclosure.

In certain embodiments, as shown in FIG. 4, provided is a watch comprising the life-saving device. Specifically, the watch comprises a strap, a dial, a case, a crown, and a movement. The wearable member comprises the housing 101 and the annular body 102 that functions as the strap. The housing further comprises an accommodation chamber to accommodate the case enclosing the dial and the movement, and the crown 18 is disposed on one side of the housing 101.

Figure 5:
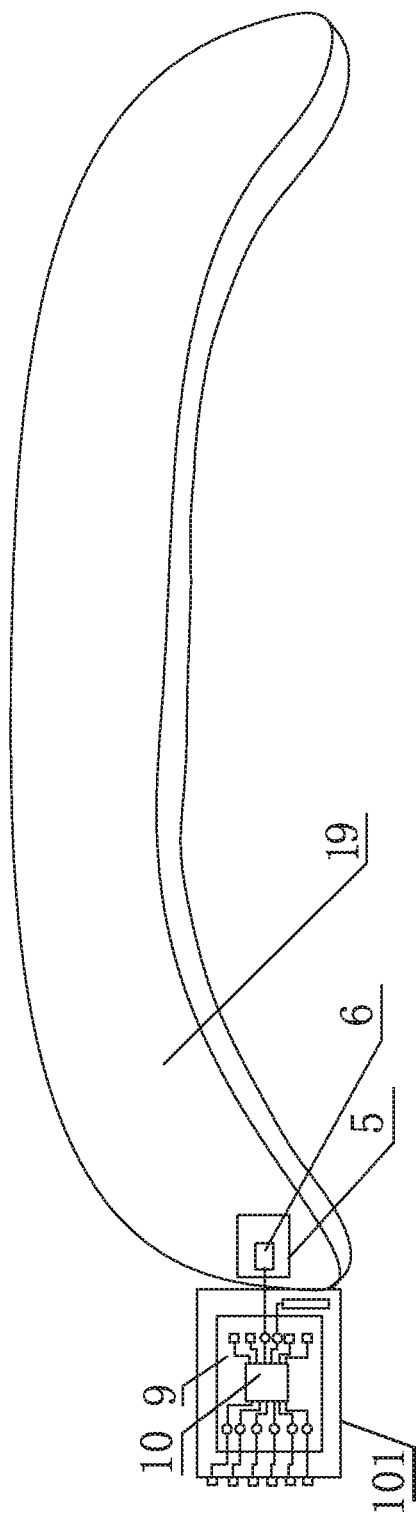
FIG. 5 is a front view of a collar comprising a life-saving device according to one embodiment of the disclosure.

Referring to FIG. 5, provided is a collar comprising the life-saving device. Specifically, the collar comprises a collar body 19 and a connector attached to clothes. The connector is a zipper. The wearable member comprises the housing 101, the collar body 19, and the connector. The collar further comprises the second chamber, and the buoyancy bag 5 that is deflated and disposed in the second chamber. The housing 101 is fixedly disposed outside the collar body 19, and comprises the first chamber, and a third chamber for mounting the display. The gas generator is fixedly disposed either in the buoyancy bag 5, or disposed outside the buoyancy bag 5 but inside the collar body 19.

In certain embodiments, the collar body 19 functions as the buoyancy bag, and the gas generator 6 is disposed in the collar body 19. The wearable member comprises the housing 101 and the connector.

Figure 6:
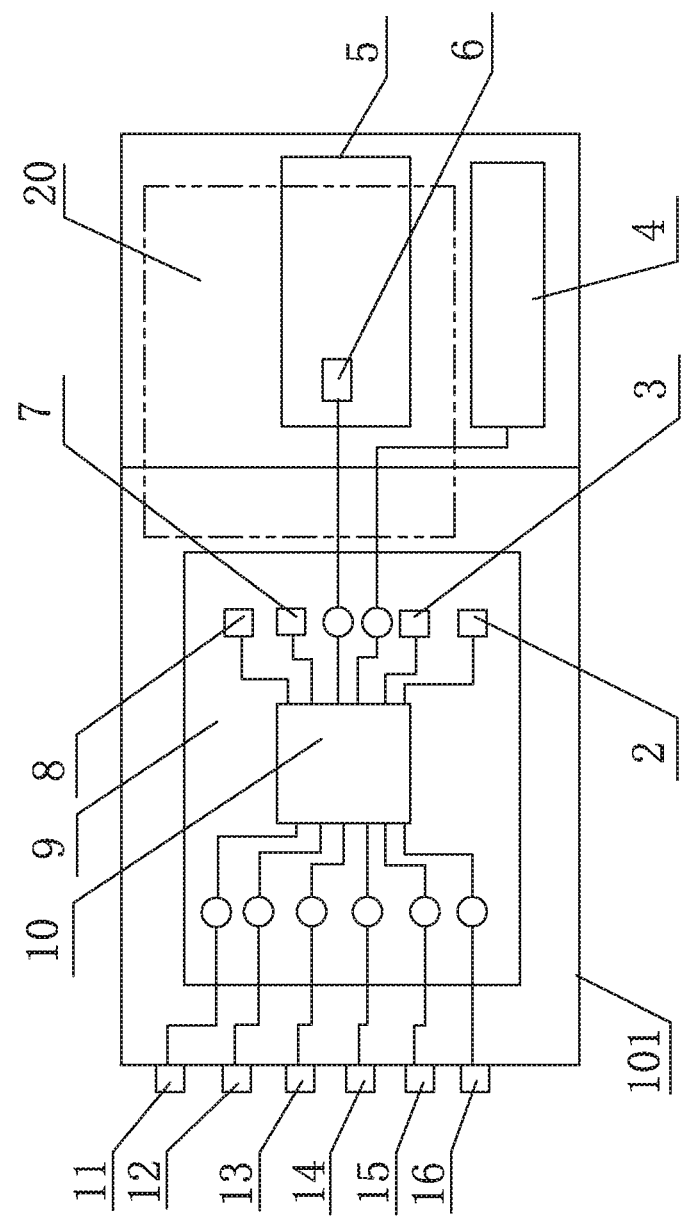
FIG. 6 is a front view of a badge comprising a life-saving device according to one embodiment of the disclosure.

Referring to FIG. 6, provided is a clothing accessory comprising the life-saving device. Specifically, the clothing accessory comprises a decoration body, and a connector connected to the decoration body and attached to the clothes. The clothing accessory is a badge, an epaulette or an armband. The connector is integrated with the decoration body to form the wearable member. The decoration body functions as the housing 101 which comprises the second chamber and a marker bar 20. The connector of the decoration is a pin, a hook-and-loop fastener, or a tear tape.

Figure 7:
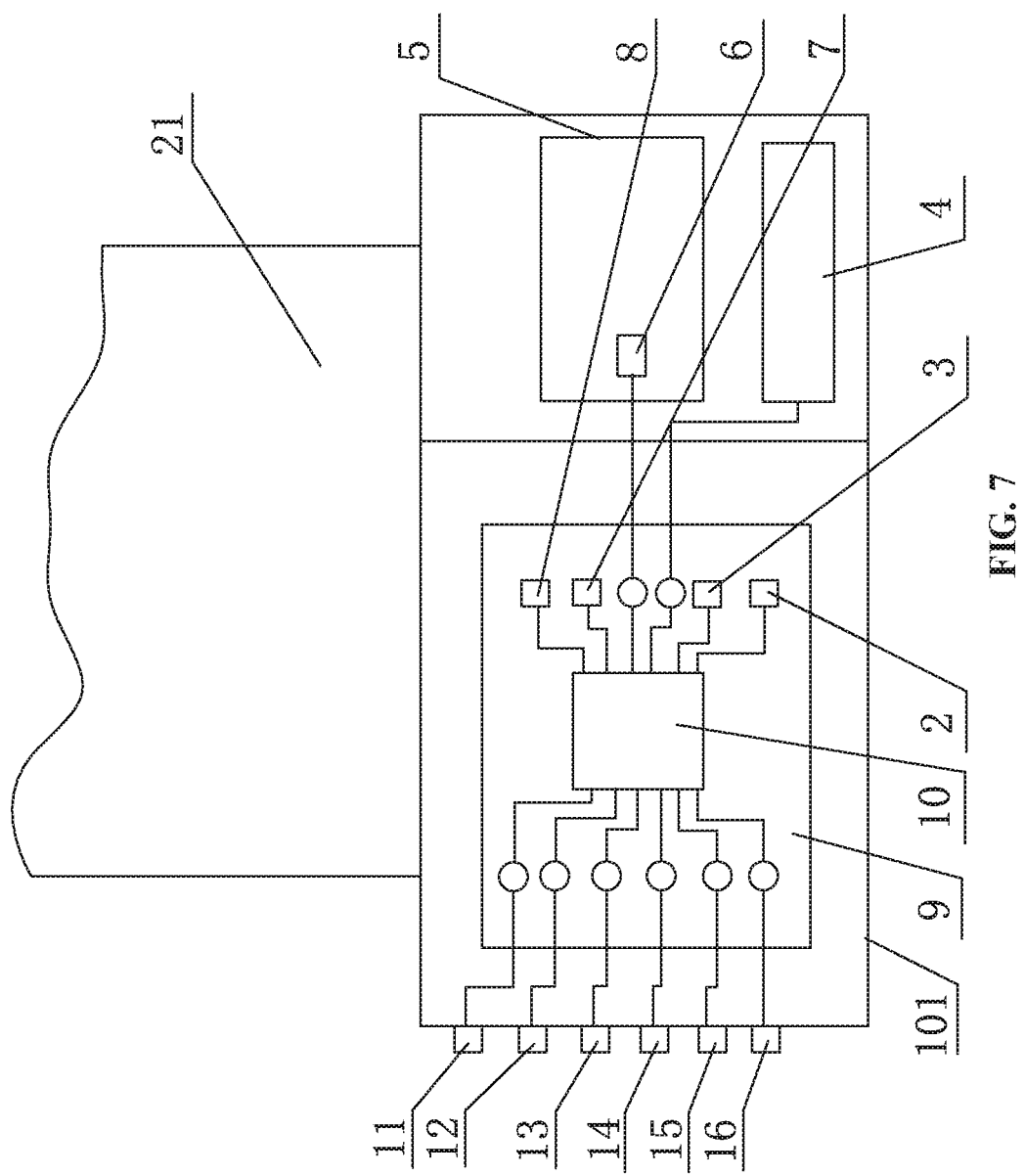
FIG. 7 is a front view of a belt comprising a life-saving device according to one embodiment of the disclosure.

Referring to FIG. 7, provided is a belt comprising the life-saving device. Specifically, the belt comprises a belt body 21 and a belt buckle. The belt buckle comprises a base disposed on the housing 101, a connecting mechanism, and a locking mechanism. The connecting mechanism and the locking mechanism are disposed on the base. The base is connected to one end of the belt body through the connecting mechanism, and comprises the first chamber and the second chamber. The base, the connecting mechanism, the locking mechanism, and the belt body form the wearable member. The belt is connected to the buoyancy bag via a rope. One end of the rope is fixedly connected to the belt body or the belt buckle of the belt. In case of emergency, the flip-flop transmits a signal to the single-chip microcomputer which determines if the gas generator generates a gas. When the gas flows into the buoyancy bag. the buoyancy bag is inflated rapidly and comes out of the second chamber, so that the inflated buoyancy bag is suspended in water and keeps the user's head and waist above water.

It will be obvious to those skilled in the art that changes and modifications may be made, and therefore, the aim in the appended claims is to cover all such changes and modifications.

What is claimed is:

1. A device, comprising:
    a buoyancy bag comprising a cavity;
    a wearable member comprising a housing;
    a controller comprising a single-chip microcomputer, a battery, a flip-flop, and an integrated circuit board; and
    a gas generator comprising an input electrode terminal and a gas outlet; wherein:
    the single-chip microcomputer comprises a plurality of pins and is disposed on the integrated circuit board;
    the battery, the flip-flop, and the input electrode terminal of the gas generator are respectively connected to the plurality of pins through the integrated circuit board;
    the housing comprises a first chamber, and the battery, the single-chip microcomputer, and the integrated circuit board are disposed in the first chamber;
    the cavity of the buoyancy bag communicates with the gas outlet; and
    the buoyancy bag is deflated when in nonuse for convenience of storage, and inflated with gas produced by the gas generator to expand in an emergency.

2. The device of claim 1, wherein the flip-flop is a pressure sensor, a delay trigger, a manual switch, or a combination thereof, and the flip-flop is disposed outside the housing.

3. The device of claim 2, wherein the gas generator comprises an electronic igniter, a gas-generating agent, and a container; the gas-generating agent is disposed in the container; the electronic igniter is disposed in the container; the gas outlet is disposed on the container; the input electrode terminal is disposed on the electronic igniter.

4. The device of claim 2, wherein the controller further comprises a low-potential alarm, a wireless signal transmitter, a solar generation mechanism, a human health monitoring sensor, or a combination thereof;
    the low-potential alarm is connected to the single-chip microcomputer via the integrated circuit board; and the low-potential alarm is disposed outside the housing;
    the wireless signal transmitter is connected to the single-chip microcomputer through the integrated circuit board; the wireless signal transmitter is disposed in the first chamber or outside the housing;
    the solar generation mechanism is disposed outside the housing; the integrated circuit hoard further comprises a power switching circuit; the solar generation mechanism and the battery are connected to the single-chip microcomputer through the power switching circuit;
    the human health monitoring sensor is disposed outside the housing and connected to the single-chip microcomputer through the integrated circuit hoard.

5. The device of claim 4, wherein the battery is a rechargeable battery.

6. The device of claim 4, wherein the wearable member comprises a second chamber, and the buoyancy bag in a deflated state is disposed in the second chamber.

7. The device of claim 6, further comprising a timer, a pedometer, or a combination thereof; wherein the timer and the pedometer are disposed in the first chamber of the housing, and connected to the single-chip microcomputer through the integrated circuit board; the device further comprises a display disposed outside the housing and connected to the single-chip microcomputer through the integrated circuit board.

8. The device of claim 7, wherein the gas generator is disposed in the buoyancy bag, or the gas generator is disposed in the second chamber but outside the buoyancy bag.

9. The device of claim 8, wherein the second chamber is disposed in the housing of the wearable member.

10. The device of claim 8, wherein the wearable member further comprises an annular body connected to the housing, and the second chamber is disposed in the housing or in the annular body.

11. The device of claim 10, wherein the second chamber and the buoyancy bag are annular in shape and match each other.

12. The device of claim 10, wherein the annular body of the wearable member is a watchstrap; the housing of the wearable member is a watchcase; the watchcase comprises an accommodation chamber to accommodate a dial and a movement.

13. The device of claim 10, wherein the annular body of the wearable member is a belt body; the housing of the wearable member is a belt buckle comprising a base, a connecting mechanism, and a locking mechanism; the base is connected to one end of the belt body via the connecting mechanism; and the first chamber and the second chamber are disposed in the base.

14. The device of claim 13, wherein the buoyancy bag is connected to one end of a rope, and the other end of the rope is fixedly connected to the belt body or the belt buckle.

15. The device of claim 9, wherein the wearable member further comprises a collar body and a connector secured to the collar body; the second chamber is disposed in the collar body; the gas producer is disposed in the buoyancy bag or disposed outside the buoyancy bag but inside the collar body.

16. The device of claim 9, wherein the wearable member further comprises a connector; the buoyancy bag is a collar body secured to the connector; and the gas producer is disposed in the collar body.

17. The device of claim 9, wherein the housing is a clothing accessory; the wearable member further comprises a connector secured to the clothing accessory; the gas producer is disposed in the buoyancy bag or disposed outside the buoyancy bag but inside the second chamber.

18. The device of claim 17, wherein the clothing accessory is a badge, an epaulette or an armband.

* * * * *